United States Patent
Hedmann et al.

(10) Patent No.: US 9,308,309 B2
(45) Date of Patent: Apr. 12, 2016

(54) METHOD FOR ACTUATING VALVES FOR CONTROLLING A FLOW PATH AND MACHINES, ESPECIALLY MEDICAL TREATMENT MACHINES

(71) Applicant: FRESENIUS MEDICAL CARE DEUTSCHLAND GMBH, Bad Homburg (DE)

(72) Inventors: Frank Hedmann, Volkach (DE); Stephan Klatte, Nienburg (Weser) (DE)

(73) Assignee: FRESENUIS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 14/570,162

(22) Filed: Dec. 15, 2014

(65) Prior Publication Data

US 2015/0165107 A1 Jun. 18, 2015

Related U.S. Application Data

(63) Continuation of application No. 14/157,322, filed on Jan. 16, 2014, now Pat. No. 8,914,156, which is a continuation of application No. 12/735,889, filed as application No. PCT/EP2009/001381 on Feb. 26, 2009, now Pat. No. 8,634,964.

(30) Foreign Application Priority Data

Feb. 29, 2008 (DE) .......................... 10 2008 011 827

(51) Int. Cl.
G05D 11/00 (2006.01)
A61M 1/28 (2006.01)
G06F 19/00 (2011.01)
G05D 7/06 (2006.01)
G06D 7/00 (2006.01)

(52) U.S. Cl.
CPC ............... *A61M 1/28* (2013.01); *G05D 7/0629* (2013.01); *G05D 7/0635* (2013.01); *G06D 7/00* (2013.01); *G06F 19/3481* (2013.01); *A61M 2205/128* (2013.01); *A61M 2205/50* (2013.01); *Y10T 137/0318* (2015.04); *Y10T 137/87096* (2015.04)

(58) Field of Classification Search
CPC ................... F15B 2211/455; F15B 2211/634; F15B 2211/6355; Y10T 137/7761; Y10T 137/86928; Y10T 137/87322; G01D 3/036; F16K 5/12
See application file for complete search history.

(56) References Cited

U.S. PATENT DOCUMENTS

| | | | | |
|---|---|---|---|---|
| 5,566,709 A * | 10/1996 | Fujii et al. | ................... | 137/487.5 |
| 6,450,254 B1 * | 9/2002 | Hoyle et al. | .................. | 165/200 |
| 6,516,249 B1 * | 2/2003 | Hoyle et al. | .................. | 700/282 |
| 6,725,130 B1 * | 4/2004 | Rogers et al. | ................. | 700/282 |
| 6,957,662 B2 * | 10/2005 | Lochtefeld et al. | ...... | 137/565.33 |

(Continued)

*Primary Examiner* — Darrin Dunn
(74) *Attorney, Agent, or Firm* — Jacobson Holman, PLLC.

(57) ABSTRACT

A method is provided for the control of valves for flow path control, in particular in a medical treatment machine, having a plurality of processes for the manufacture of flow paths by control of a group of valves, with each process claiming a group of valves suitable for its carrying out for itself so that other processes cannot change the switching state of these valves and with each process itself making a decision on the release of the valves claimed by it. In addition, a method is provided for monitoring the then current and/or scheduled state of a plurality of valves in the flow path control, determining the connections resulting from the switching state of the valves, and comparing the resulting connections with a predetermined number of non-permitted connections.

23 Claims, 8 Drawing Sheets

(56) References Cited

U.S. PATENT DOCUMENTS

| | | |
|---|---|---|
| 7,720,574 B1 * | 5/2010 | Roys .................... 700/282 |
| 8,032,258 B2 * | 10/2011 | Ludwig .................... 700/282 |
| 8,127,063 B2 * | 2/2012 | Sherriff et al. ............ 710/244 |
| 2001/0025232 A1 * | 9/2001 | Klimasauskas et al. ........ 703/13 |
| 2007/0294450 A1 * | 12/2007 | Rudnick et al. .............. 710/244 |
| 2008/0098401 A1 * | 4/2008 | Weatherhead et al. ....... 718/104 |
| 2009/0088905 A1 * | 4/2009 | Parraga .................... 700/282 |
| 2010/0082145 A1 * | 4/2010 | Weatherhead et al. ....... 700/106 |
| 2011/0028882 A1 * | 2/2011 | Basaglia .................... 604/4.01 |
| 2012/0016494 A1 * | 1/2012 | Pettus et al. .................... 700/9 |

* cited by examiner

METHOD FOR ACTUATING VALVES FOR CONTROLLING A FLOW PATH AND MACHINES, ESPECIALLY MEDICAL TREATMENT MACHINES

This is a continuation application of U.S. patent application Ser. No. 12/735,889, filed Aug. 24, 2010, issuing as U.S. Pat. No. 8,634,964 on Jan. 21, 2014, which was a national stage of PCT/EP2009/001381 filed Feb. 26, 2009 and published in German, which had a priority of German application no. 10 2008 011 827.3 filed Feb. 29, 2008, and hereby claims the priority thereof to which it is entitled.

BACKGROUND OF THE INVENTION

1. Field of the Invention

The present invention relates to a method for the control of valves for flow path control, in particular in a medical treatment machine. The present invention furthermore relates to a method for the monitoring of the then current and/or scheduled state of a plurality of valves in flow path control, in particular in a medical treatment machine, as well as to a machine, in particular a medical treatment machine, having a control for the carrying out of the corresponding methods.

The present invention in particular relates to methods for the operation of a machine in which a cassette system is used for the transport of liquids, in particular medical liquids. The present invention is used particularly advantageously in treatment machines in the field of dialysis, in particular in the field of peritoneal dialysis. Cassette systems are usually used in such treatment machines for the transport of the treatment liquids or for the carrying out of the treatment.

The present invention in particular relates to peritoneal dialysis machines such as are presented in US 2007/0112297 A1 and US 2006/0195064 A1 as well as to methods for the operation of such peritoneal dialysis machines. The full extent of the content of 2007/0112297 A1 and US 2006/0195064 A1 is hereby an integral part of the disclosure of the present application.

2. Description of the Related Art

The disposable cassettes used in such cassette systems have fluid paths and valve points via which the flow paths required for the respective treatment step can be established in the cassette. The fluid paths of the cassettes are usually formed by liquid conducting passages which have at least one flexible wall in the region of the valve points. The flexible wall can then be pressed into the liquid conducting passage by a valve actuator and so block said passage. Pneumatically actuable actuators can e.g. be used as the actuators which expand on the application of pressure to the actuator and so serve as valve tappets. Hydraulic or electric motor valve actuators can equally be used. The liquid conducting passages with the valve points are usually arranged at the disposable cassette; the valve actuators at the treatment machine. The cassettes are then inserted into the treatment machine and coupled to it so that the valve actuators at the treatment machine come into engagement with the valve points at the cassette and determine the switching state of the valves of the cassette.

Programs are usually stored in the machine control for the control of the valves and the group of valves required for the establishing of a required flow path (e.g. from a pump chamber to the patient) are controlled via said programs. A flow path is in this context understood as the connection between two sources and/or sinks which are connected by valves, e.g. the connection between a bag and a pump which is established by opening the valves disposed between the bag and the pump as well as closing valves to other component conducting connection lines. A plurality of valves are usually provided, e.g. nine or sixteen valves in known systems, via whose different control a plurality of different flow paths between the patient, the pump chambers of the cassette and different bags with liquid or for drainage can be established.

In known methods, a flow path which is e.g. required for a certain pump cycle is fixedly predetermined by the method used. In this connection, the machine knows the corresponding flow path for the method used since it is fixedly stored in the application. If the method now requires a connection from a point A to a point D, which could theoretically take place both via B and via C, this connection is previously stored in the application—e.g. via B. The application therefore does not have a free choice, but rather has a fixedly stored connection assigned to it in the present case.

A monitoring of the permitted flow path A-B-D is not necessary in this respect since only permitted and previously fixed connections are stored in the protection system. The flow paths required for a complete application are thus stored on the programming of the methods. If now a new method should be integrated into the application of the machine, the flow paths required for this must be checked as to whether they are stored in the protection system or whether they have to be stored as new, which has to result in a total check since the change between individual flow paths to be switched possibly also has to be checked for meaningfulness. A further disadvantage of the previously known systems is furthermore the change between two preset pump cycles since all the valves first have to be closed for this purpose for safety reasons. This results in an increase in wear in the valve components. The known systems are therefore inflexible and make the implementation of new methods difficult.

SUMMARY OF THE INVENTION

It is the object of the present invention to provide methods for the control or monitoring of valves for flow path control in which the implementation of new methods is made more flexible, with the necessary safety aspects nevertheless being taken into account. It is furthermore the object of the present invention to provide machines, in particular medical treatment machines, having corresponding valve controls or valve actuator controls.

This object is solved by a method for the control of valves for flow path control, in particular in a medical treatment machine, having a plurality of processes for the establishing of flow paths by controlling a group of valves, wherein each process claims a group of valves suitable for its carrying out for itself so that other processes cannot change the switching state of these valves; and wherein each process itself makes a decision on the release of the valves claimed by it. This object is also solved by a method for the monitoring of the then current and/or scheduled state of a plurality of valves in the flow path control, in particular in a medical treatment machine, having the steps of determining the then current and/or scheduled switching state of the valves; determining the connections resulting from the switching state of the valves; and comparing the resulting connections with a predetermined number of non permitted connections.

The object is further solved by a machine, in particular a medical treatment machine, having a plurality of valve actuators for the control of valves for the flow path control, in particular in a cassette system, with a valve actuator control for the carrying out of a plurality of processes for establishing flow paths by controlling a group of valve actuators, with the valve actuator control being configured such that each process claims a group of valve actuators suitable for its carrying out for itself so that other processes cannot change the switching state of these valve actuators and each process itself makes a decision on the release of the valve actuators claimed by it. Still further, the object is solved by a machine, in particular a medical treatment machine, having a plurality of valve actuators for the control of valves for the flow path control, in particular in a cassette system, having a valve actuation control and having a monitoring unit for the monitoring of the then current and/or scheduled state of a plurality of valves, with the monitoring unit determining the then current and/or scheduled switching state of the valves and the connections resulting from the switching state and comparing the resulting connections with a predetermined number of non permitted connections.

The present invention includes a method for the control of valves for flow path control, in particular in a medical treatment machine, having a plurality of processes for the manufacture of flow paths by control of a group of valves, with each process claiming a group of valves suitable for its carrying out for itself so that other processes cannot change the switching state of these valves and with each process itself making a decision on the release of the valves claimed by it. It is possible, on the one hand, by this method to allocate valves or groups of valves to individual processes in a flexible manner.

In this context, a process represents a method constituent within the valve control of the machine which provides a certain flow path. For this purpose, a process requires a group of valves whose switching state it sets thus that the valves establish the flow path. This group of valves usually only represents some of all the valves so that a process usually does not claim all valves for its carrying out. In this connection, there can be a plurality of different possibilities of realizing a flow path for the same flow path, e.g. from a pump chamber to a bag, i.e. a process can be realized by different groups of valves.

It is now possible by the method in accordance with the invention that individual processes flexibly claim different groups of valves without impairing the safety of the system. While one process claims the group of valves required for the establishing of the flow path, other processes cannot change the switching state of these valves so that only the process providing a flow path can also make a decision on its cancellation.

In this context, each process makes a decision on the release of the valves claimed by it in accordance with internal and/or external process criteria. Internal process criteria can e.g. be pump positions, steps already carried out or the completion of the process. External circumstances can e.g. be a higher prioritization of another process. It is, however, decisive in the present method that only the process respectively claiming the valves can also release them again so that a coordinated and reliable interplay of a plurality of processes is ensured.

In this connection, each process advantageously releases the claimed group of valves after its ending. These valves can hereby in turn again be claimed by other processes and used for carrying them out.

Advantageously, a process can in this connection claim different groups of valves depending on the availability of the valves. This enables a flexible valve management in which the available resources are ideally utilized. In this connection, in a first method variant, a valve is considered as available for a process if it is not claimed by any other process. A valve can thus, however, always only be claimed by a single process even if two processes actually require the same switching state for a valve and are therefore basically compatible.

In a second method variant, a valve is therefore considered as available for a second process when it is not claimed by any other process or when it is admittedly already claimed by a first process, but has the switching state required by the second process. The switching state of such a valve already claimed by a first process can no longer be changed by the second process in this connection. If this is, however, not necessary for the establishing of the flow path by the second process, the second process can then use this valve. For this purpose, the second process advantageously also claims the valve so that its switching state can also no longer be changed by the first process. Both processes can thus utilize the same valve, with an unintentional cancellation of the flow path of the one process by the other process being prevented by the claiming of the valve.

In this connection, the individual processes advantageously represent method constituents within the valve control of the machine which establish a specific flow path and maintain it up to their end. The changing of a flow path thus always takes place by the carrying out of a new process.

In this connection, in accordance with the invention, each process advantageously polls the availability of a group of valves suitable for its carrying out before its carrying out. A process which wants to establish a certain flow path thus initially polls whether a group of valves suitable for this purpose is already available.

A process is advantageously carried out in this connection when a suitable group of valves is available, with the process claiming this group of valves for itself. If therefore such a group of valves is available, the process can be carried out independently of further processes possibly running in parallel. It is sufficient for this purpose for a combination of valves to be available from a plurality of possible combinations of valves which are suitable for the establishing of the desired flow path. If, however, the desired flow path cannot be established with the available valves, the process can thus initially not start.

Advantageously, the polling of a non-available valve by a second process results in a request to the first process claiming this valve to release this valve, with only the first process making a decision on this request. This is in particular the case if no suitable group of valves is available for the carrying out of the second process. The second process then requests the first process to release the valve it needs. The first process now makes an independent decision on this request, with internal and external process criteria being able to be taken into account. Only when the first process has released the required valve or the required group of valves can the second process change their switching state and establish the desired fluid path.

In this connection, the polling process advantageously claims all of the polled and available valves for itself. It is hereby ensured in a plurality of processes that a process can initially claim all the available valves for itself and thus only has to wait for the valves which have to be released by other processes so that it can change their switching state.

Advantageously, the polling process furthermore receives a right to claim all polled but not available valves on the polling so that it can claim these valves for itself when they have been released. A reliable transition from one process to the next is hereby possible even with a plurality of processes. In particular different priority rights can be awarded for different processes in this connection.

Advantageously, the method in accordance with the invention includes a central valve allocation process in which all the other processes claim, release and/or request the required valves. This central valve allocation process thus takes over the distribution management for the individual valves and valve groups, with the release of individual valves, however, only being able to take place by the process which is then currently utilizing them.

The method in accordance with the invention advantageously includes the following steps: claiming a first group of valves for the carrying out of a first process in which a first flow path is established by control of the associated first group of valves; polling the availability of a second group of valves for the carrying out of a second process in which a second flow path should be established by control of the associated second group of valves; and carrying out the second process when all required valves are available, with the polling of valves which are not available by the second process resulting in a request to the first process to release these valves, with only the first process making a decision on this request.

The present invention thus permits a flexible flow path planning. A flow path in this connection is understood as the connection between two sources and/or sinks which are connected by valves, e.g. the connection between a bag and a pump. If such a flow path is made available by a first process, the valves controlled for this purpose are claimed by this first process and their switching state of can no longer be changed by further processes to establish other flow paths. If now a specific flow path is requested by a second process, e.g. by a second pump cycle of the process, all the valves required for the flow path are then polled. The available valves can be claimed. The valves which are already assigned to the first process, e.g. a first pump cycle, and whose switching state would have to be changed, are requested in this first process. The first process has sole power of decision on when and if it releases the valves to the second process. As soon as the corresponding valves have been released by the first process, the requesting second process can use the valves and form its flow path.

To prevent an unwanted free flow on a change from a first process to a second process, the required valves which are already in the correct state for the corresponding process are left in their state. It applies to the valves whose state has to be changed that the valves to be closed are closed in a first step. In a second step, the valves required by the second process in an open state are opened.

It is possible by this method in accordance with the invention for the control of the valves that a plurality of processes access the individual valves in a flexible manner, with a reliable operation nevertheless being ensured by the release rules in accordance with the invention. This flexible and open architecture of the processes in accordance with the invention makes it possible to implement new processes particularly simply. In particular the complete system architecture no longer has to be revised for this purpose. It is rather the case that new processes can be added to the existing processes without problem.

There are thus additionally substantially fewer valve switching processes and thus a lower wear of the valve components by this type of the flow path formation in the flexible design of the implementation of new processes which can run on the treatment machine, e.g. a cycler. Such a cycler represents a treatment machine for dialysis, in particular for peritoneal dialysis, which permits an automated exchange of the dialysis liquids. It is in particular possible to dispense with initially closing all valves on a change between pump cycles, as is still necessary in the prior art for safety reasons.

The present invention in this connection furthermore includes a machine, in particular a medical treatment machine, having a plurality of valve actuators for the control of valves for the flow path control, in particular in a cassette system, with a valve actuator control for the carrying out of a plurality of processes for establishing flow paths by controlling a group of valve actuators, with the valve actuator control being configured such that each process claims a group of valve actuators suitable for its carrying out for itself so that other processes cannot change the switching state of these valve actuators and each process itself makes a decision on the release of the valve actuators claimed by it. Valves which are in particular arranged in a cassette system which is inserted into the machine are controlled via the valve actuators to make corresponding flow paths available in the cassette. The same advantages result from such a machine such as were already described with respect to the method. It is in particular hereby possible to associate different groups of valve actuators to the individual processes in a flexible manner without impairing the safety of the system. The valve actuator control in accordance with the invention is in particular programmed such that the processes in accordance with the invention can be carried out in accordance with the invention, with the method in accordance with the invention advantageously running automatically on the machine in accordance with the invention.

In this process, in accordance with the invention, each process advantageously makes a decision on the release of the valve actuators claimed by it in dependence on internal or external process criteria. As already described with respect to the method, the safety of operation of the machine is hereby ensured.

In this connection, each process advantageously releases the claimed group of valve actuators after its end. The latter can thereby again have their switching states changed by other processes.

In this connection, a process can advantageously claim different groups of valve actuators in dependence on the availability of the valve actuators. A flexible association of different groups of valve actuators to a process is hereby possible so that different groups of valve actuators can be controlled by the same process for the establishing of a flow path.

Each process advantageously polls the availability of a group of valve actuators suitable for its carrying out before its carrying out. A process is carried out in this connection when a suitable group of valve actuators is available, with the process claiming this group of valve actuators for itself. It is hereby ensured that other processes can no longer change the switching state of this group of valve actuators so that only the process itself can make a decision whether the flow path provided by it is maintained or cancelled.

Advantageously, the polling of a non-available valve actuator by a second process results in a request: to the first process claiming this valve actuator to release this valve actuator, with only the first process making a decision on this request. A poll in particular results in a request to release a valve actuator when no group of valve actuators is available with which the second process could establish the intended flow path. In this case, the flow path provided by the first process first has to be cancelled to be able to form the flow path to be provided by the second process.

In this connection, the polling process advantageously claims all of the polled and available valve actuators for itself. The available valve actuators, that is all the valve actuators not claimed by another process and, advantageously, all the valve actuators claimed by other processes, but already being in the desired switching state, can hereby be claimed by the polling process for itself so that the switching process of these valve actuators can no longer be changed by other processes.

Further advantageously, the polling process furthermore receives a right to use with respect to all polled but not available valve actuators on the polling so that it can claim these valve actuators for itself when they have been released. If therefore the switching state of a valve actuator already claimed by another process has to be changed, the polling process does not claim this valve for itself, but only receives a claim right to it which it can exercise when this valve actuator has been released by the first process. A synchronization of a plurality of different processes is hereby possible.

The valve actuator control advantageously includes a central valve association process in which all the other processes can claim, release and/or poll the required valve actuators.

The valve actuator control in accordance with the invention is advantageously programmed such that the following steps can be carried out: claiming a first group of valve actuators for the carrying out of a first process in which a first flow path is established by control of the associated first group of valves; polling the availability of a second group of valve actuators for the carrying out of a second process in which a second flow path should be established by control of the associated second group of valves; and carrying out the second process when all required valve actuators are available, with the polling of valve actuators which are not available by the second process resulting in a request to the first process to release these valve actuators, with only the first process making a decision on this request.

The machine in accordance with the invention advantageously has a coupling surface for the coupling of a cassette, with the cassette including passages having valves and conducting liquids and with the valve actuators on the machine side for the establishing of different flow paths in the cassette determining the switching state of the valves on the cassette side. In this connection, the valve actuators are advantageously arranged on the coupling surface of the machine. The cassette usually represents a disposable part which is inserted into the machine.

In accordance with the invention, a method thus results as well as a corresponding machine on which the flow path formation can be implemented with much greater flexibility.

The safety system should also be adapted to the flexible flow path planning in accordance with the invention, in particular in order not to lose the flexibility gained in the flow path planning again.

The present invention therefore furthermore includes a method for the monitoring of the then current and/or scheduled state of a plurality of valves in the flow path control, in particular in a medical treatment machine, having the steps: determining the then current and/or scheduled switching state of the valves; determining the connections resulting from the switching state of the valves; and comparing the resulting connections with a predetermined number of non-permitted connections.

All the permitted flow paths are therefore no longer stored, which would then have to be revised on a change or a new introduction of a method, but rather all the prohibited paths are determined and stored once for the total arrangement of the valves, pumps and connections, that is for all the valves, sinks and/or sources of the system. Only the connections resulting from the switching state of the valves thus still have to be determined and compared with this number of non-permitted connections for the monitoring of the then current and/or scheduled state of the valves or of the system.

Only connections between the inlets or outlets of the system have to be taken into account as non-permitted connections, e.g. a connection between the terminal leading to the patient and the terminal leading to the drainage bag. The internal switching state of the valves, which corresponds to one of such connections, in contrast no longer has to be classified as permitted or non permitted since the method determines which connections are present between the inlets and outlets of the system by the switching state of the valves (and the internal connections connected thereto). Only these connections between the inlets and outlets of the system then have to be compared with the non permitted connections.

The determination of the connections resulting from a switching state advantageously always takes place when the switching state of a valve changes or should change. The valve states are therefore monitored. If the valve state changes or if a process wants to change a valve status, the connections or flow paths resulting from the changed switching state of the valve are determined and a check is made whether these connections or flow paths are non permitted connections or flow paths.

In this connection, all the open valves are advantageously virtually flooded, starting from one or more starting points, for the determination of the connections resulting from a switching state. In this connection, a check is made, starting from one starting point, as to which connections result over the open valves of the system starting from this starting point. In this connection, the valves and the connections resulting through the passages conducting liquid between the valves are stored, e.g. in the form of a network, in the treatment machine.

An open, not yet flooded valve is advantageously respectively selected as the starting point in this connection. Starting from this open, not yet flooded valve, all the open valves connected to this valve are then virtually flooded from which, in turn, all the adjacent open valves are flooded until no further adjacent open valves are found which have still not been flooded. At the end of this process, the connection between a plurality of sources and/or sinks established by the respectively flooded connections then results. If the system still has further open, not yet flooded valves, the process is continued with one of these valves as the starting point to determine all the connections established by the system.

Advantageously, in this process, in accordance with the invention all the determined connections are entered in a connection matrix. It can, in particular, be entered into such a matrix for all combinations of valves of the total system whether a connection is present between these two valves or not by the then current switching state of the valves. In this regard, an iterative procedure can in turn be followed, as described above, in that all the open valves are virtually flooded sequentially, starting from one or more starting points, and the connections resulting therefore are entered into the connection matrix.

In this way, only the resulting connection matrix has to be compared with a control matrix in which all the non permitted connections have been entered. If the resulting connection matrix has no entry which would correspond to a non permitted connection, the connections provided by the then current and/or scheduled state of the valves are permitted.

If, in contrast, a non permitted connection is recognized for a switching state of the valves, safety measures are initiated. If the method recognizes a non permitted connection for a current switching state, the system advantageously switches into a safe state. Upon recognition of a non permitted connection which would result from a scheduled switching state of the valves, this switching state is not brought about.

In accordance with the invention, an extremely safe method hereby results for the monitoring of the valves by which it is ensured that no non permitted flow paths are established. Since the non permitted flow paths only have to be preset once, the safety system does not have to be adapted to newly implemented processes and thus has the high flexibility of the system in accordance with the invention.

The present invention furthermore includes a machine, in particular a medical treatment machine, having a plurality of valve actuators for the control of valves for the flow path control, in particular in a cassette system, having a valve actuator control and having a monitoring unit for the monitoring of the then current and/or scheduled state of a plurality of valves, with the monitoring unit determining the then current and/or scheduled switching state of the valves and the connections resulting from the switching state and comparing the resulting connections with a predetermined number of non permitted connections. The machine in accordance with the invention is in particular equipped with a control which is programmed so that the method in accordance with the invention for the monitoring of the valve position is carried out on it, in particular automatically. Advantageously, the switching state of a valve is determined by the switching state of the associated valve actuator of the machine so that the monitoring of the switching state of the valve actuators on the machine side can be used for the monitoring of the switching state of the valves. The valves themselves are, in contrast, usually components of a cassette which is inserted into the machine as a disposable part.

A flexible capability of reliably monitoring the switching state of the valve actuators or valves and thus the permissibility of the then current and/or scheduled flow paths thus results with the machine in accordance with the invention.

The determination of the connections resulting from a switching state advantageously always takes place when the switching state of a valve changes or should change. The machine in accordance with the invention thus always checks the permissibility of the connections when a valve actuator is controlled or should be controlled.

In this connection, all the open valves are advantageously virtually flooded, starting from one or more starting points, for the determination of the connections resulting from a switching state. The machine in accordance with the invention advantageously includes a memory in which a representation of the valves and of the flow paths is stored. The machine furthermore advantageously includes a computing unit which carries out a virtual flooding on the basis of these data.

An open, not yet flooded, valve is advantageously respectively selected as the starting point in this connection. Further advantageously, all the connections determined are entered into a connection matrix. For this purpose, the machine in accordance with the invention advantageously has a memory in which the determined connections can be stored.

Further advantageously, the resulting connection matrix is compared with a control matrix in which all non permitted connections have been entered. The machine in accordance with the invention also advantageously has a memory for this purpose in which the control matrix is stored. The monitoring unit then advantageously compares the resulting connection matrix with the stored control matrix.

In this regard, the machine advantageously switches into a safe state on recognition of a non permitted connection with a then current switching state of the valves and/or does not initiate this switching state on recognition of a non permitted connection with a scheduled switching state. The safety of the machine is hereby guaranteed.

The machine in accordance with the invention advantageously has a coupling surface for the coupling of a cassette, with the cassette including passages having valves and conducting liquids and with the valve actuators on the machine side for the establishing of different flow paths in the cassette determining the switching state of the valves on the cassette side.

As described, both the method in accordance with the invention for the control of the valves and the method in accordance with the invention for the monitoring of the state of the valves are of great advantage independently of one another. It is, however, obvious to the skilled person that particularly the combination of the extremely flexible control method with the equally flexible monitoring method results in special advantages, in particular on the implementation of new processes.

The present invention furthermore includes a machine, in particular a medical treatment machine, having a plurality of valve actuators for the control of valves for flow path control, in particular in a cassette system, with the machine having a control for the carrying out of one of the methods described above. The control in accordance with the invention is in particular programmed such that one or more of the methods in accordance with the invention can be carried out. The same advantages hereby evidently result such as were already described above with respect to the method.

Furthermore, the present invention includes a computer program product, in particular a memory medium with a computer program, for transferring to a machine, in particular to a medical treatment machine, with commands for the carrying out of a method such as are described above. An existing machine, in particular an existing medical treatment machine, on which methods in accordance with the prior art have previously been used, can be put in a position by such an update to carry out the methods in accordance with the invention.

BRIEF DESCRIPTION OF THE DRAWINGS

The present invention will now be described in more detail with reference to embodiments and drawings. There are shown:

FIGS. 9*a*-9*d* are individual steps in the preparation of a connection matrix by the embodiment of the method in accordance with the present invention for the monitoring of a state which correspond to the steps shown in FIGS. 6*a* to 6*d*.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
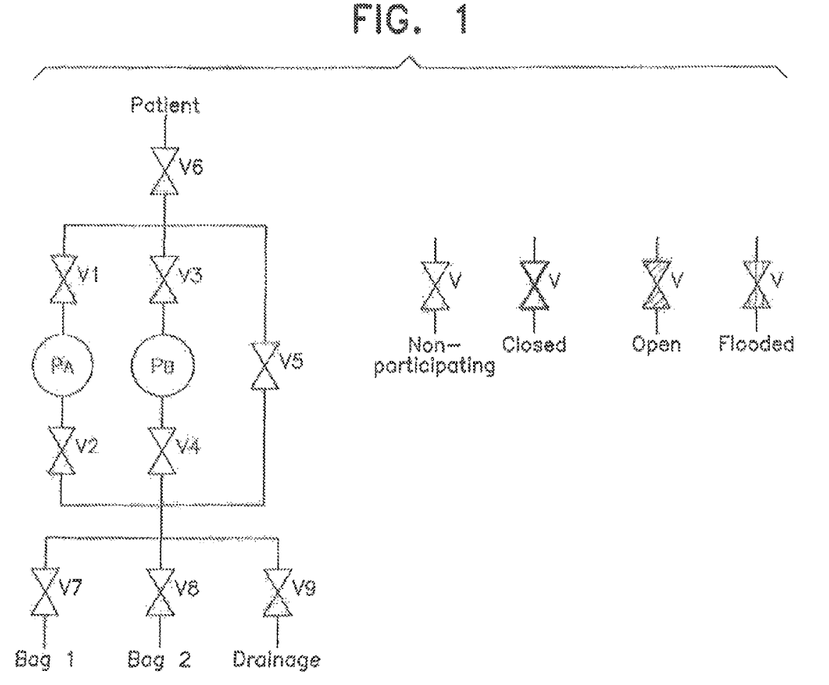
FIG. 1 is a valve arrangement for whose control and/or monitoring embodiments of the methods in accordance with the invention are used as well as a legend for the symbols used in the drawings following it.

In FIG. 1, a valve arrangement is shown for whose control and/or monitoring the methods in accordance with the invention can be used. The fluid paths and valves shown are integrated in a disposable cassette which is inserted into a treatment machine in accordance with the invention and is there coupled to a coupling surface. The coupling surface of the treatment machine has valve actuators which cooperate with valve points at the cassette and hereby form valves.

The fluid paths in the cassette are formed by liquid conducting regions which have flexible walls at least in the region of the valve points. The flexible regions can be pressed by the valve actuators into the regions conducting liquid to close said regions. The cassette in particular consists of a hard part with liquid conducting passages which are covered by a flexible foil. The disposable cassette furthermore has, beside the fluid paths and the valves, pump chambers PA and Ps which are likewise formed as liquid conducting regions covered by a flexible membrane, with the membrane being able to be pressed into or out of the cassette by the treatment machine so that a pump function results.

In the valve system shown in FIG. 1, a plurality of inlets and outlets are provided which can be connected to one another and/or the pump chambers via the valves. Connections for liquid bags and for the patient are in particular provided. Each of the connections for external lines has its own valve. Furthermore, respective valves are provided at the inlets and outlets of the two pump chambers PA and P8.

The pump chambers are thus in communication with the patient connection via valves V1, V3 and V6. Furthermore, the pump chambers are in communication with the liquid bags via valves V2, V4 and V7 to V9. The patient connection is likewise directly in communication with the liquid bags via the valve V5. In this connection, in the arrangement shown in FIG. 1, two connections are provided for liquid bags for treatment liquids as well as one connection for a drainage bag.

The two pump chambers are arranged parallel to one another between a common line which leads to the liquid bags and a line which leads to the patient. Furthermore, a line having the valve V5 and parallel to the pump chamber is provided via which a direct connection can be established between the patient and the liquid bags.

Embodiments of the methods in accordance with the invention for the control of the valves V1 to V9 as well as for their monitoring will now be described in more detail with reference to FIGS. 1 to 9. For this purpose, the symbols shown in FIG. 1 will be used for the different switching states of the valves. A valve filled in in white stands for a non-participating valve whose switching state with respect to the corresponding method is not defined. A valve filled in in black stands for a closed valve; a valve filled with diagonal hatching stands for an open valve. A valve filled with vertical hatching, in contrast, stands for an open valve which has been virtually flooded for the method.

In this connection, a starting position of a method for controlling valves for flow path control of a medical treatment machine is shown in FIG. 1. All the valves are initially non participating, that is they can be mechanically open or closed. Since a certain starting status is required for the control of the flow paths, the valves are initially closed in the embodiment.

Figure 2A:
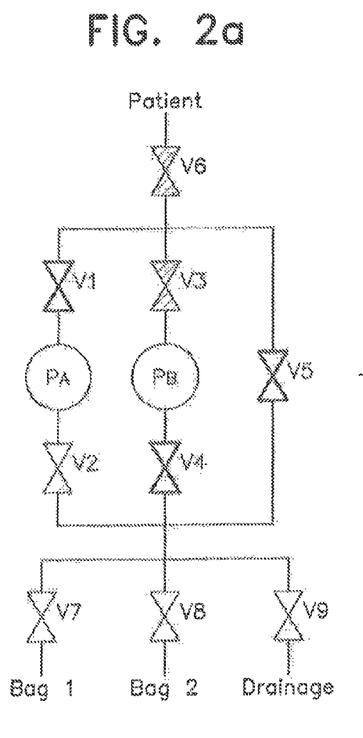
FIG. 2a is a first process which is used in an embodiment of the method in accordance with the present invention for the control of valves.

The embodiment of the method in accordance with the invention includes a plurality of processes for the establishing of flow paths by the control of a group of valves, with each process claiming the respectively required group of valves for itself during its carrying out so that other processes cannot control these valves. In FIG. 2*a*, a first process 8 is shown which establishes the flow path from the patient to the pump P8. The valves V1, V4 and V5 are closed for this purpose, while the valves V3 and V6 are open. All other valves remain non participating. The process shown in FIG. 2*a* thus claims the valves V1, V3 and V4 to V6 for itself so that other processes cannot change the switching state of these valves.

Figure 2B:
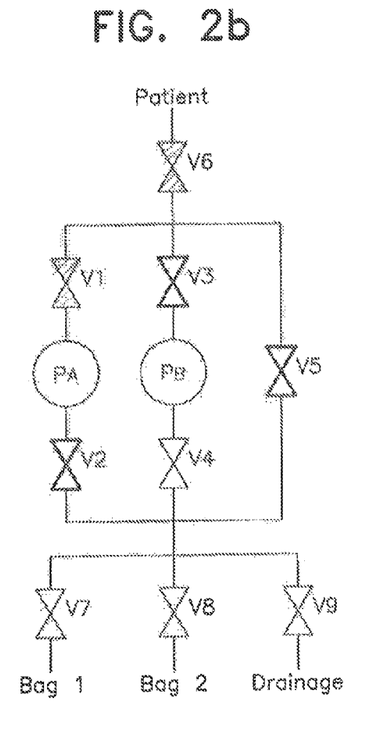
FIG. 2b is a second process which is used in an embodiment of the method in accordance with the present invention for the control of valves.

In FIG. 2*b*, a second process A is now shown by which a flow path from the patient to the pump chamber PA should be established. For this purpose, the valves V2, V3 and V5 are closed and the valves V1 and V6 are open, while the other valves remain non participating. The second process A thus requires the valves V1 to V3 as well as V5 and V6. With the exception of the valve V2, however, all these valves are still reserved by the first process 8 so that process A cannot control them. The valve V3 reserved by the first process is in particular in its open position, while it would have to be closed for the second process. The query made by the second process whether the valves required for the establishing of the desired flow path are available thus has the result that the required valves are partly reserved by another process since valve 3 is claimed by the first process and its switching position would have to be changed.

The second process thus initially only reserves the already available valves which are needed to provide the fluid path, i.e. the still unclaimed valve V2 and the valves V1, V5 and V6 which are claimed by the first process and which are already in the switching state required by the second process, and makes a request to the first process so that it releases the valves still needed. The first process then decides whether and when it will release the required valves, i.e. the valve V3 which would have to be switched over. The second process must wait so long. The decision of the first process on the release of the requested valves can be influenced by its own process criteria such as the pump position or by external circumstances such as a higher prioritization of the other process. It is, however, decisive in this connection that only the first process can release the valves used by it. A cooperation of the process is hereby ensured which is as safe as it is coordinated. In accordance with the invention, accordingly only the process which has claimed a specific valve at the then current time can also release it again.

Figure 3:
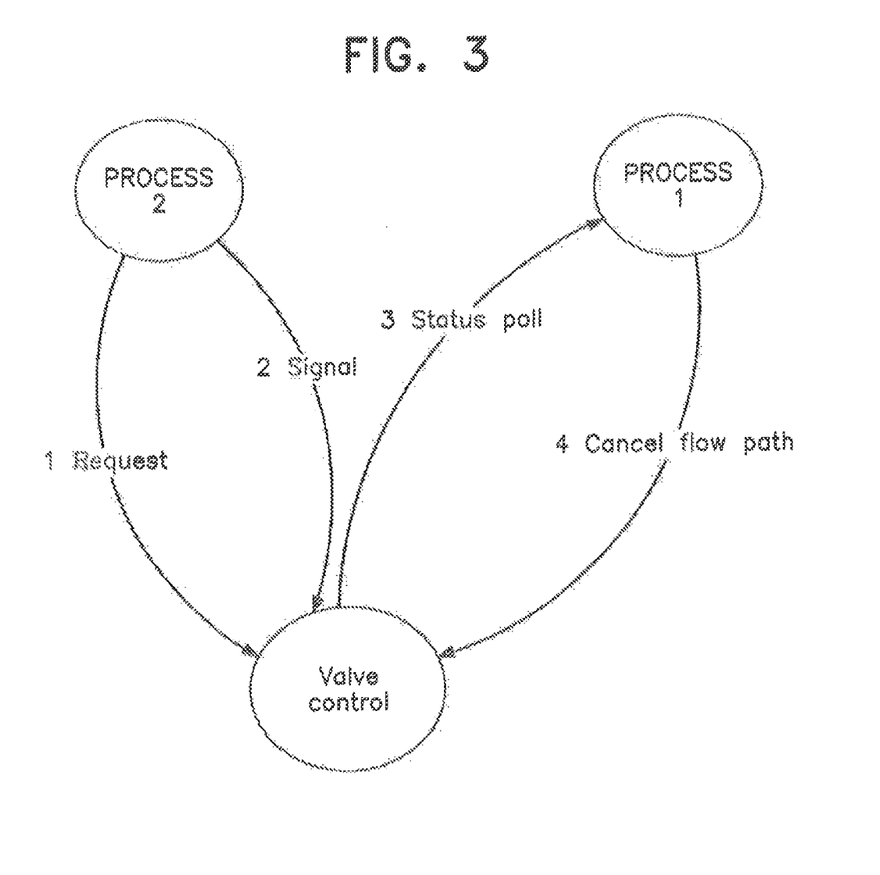
FIG. 3 is a diagrammatic representation of the embodiment of the method in accordance with the present invention for the control of the valves.

The procedure of the routine of the method in accordance with the invention for the control of the valves will be presented in more detail again with reference to the process diagram shown in FIG. 3. The process 1 has established a certain flow path and claims a first group of valves for this purpose. The second process 2 now first polls the availability of a second group of valves by whose control a second flow path should be established. This polling of the available valves simultaneously represents a request to the central valve control to associate these valves with the second process. In this connection, the second process can, however, only claim those valves for itself by its poll which are available. The second process can only obtain a claim right from the valve control for the polled valves which are not available so that it can claim these valves for itself when they are released. It can hereby be prevented that a third process claims the valves required by the second process, but not yet released, for itself when they are released.

The second process now signals to the first process via the valve control with respect to the polled but not yet available valves and thus requests the first process to release the required valves. The process 1 can here detect, e.g. with the help of a status query (polling), that the valves are needed and the flow path formed by process 1 should be cancelled. The first process can now make a free decision on how to proceed. In particular only the first process makes a decision on the request whether the valves requested by the second process and claimed by the first valves will be released or not. If the first process releases the valves, it reports this to the central valve control. All the valves required for the second process are hereby available so that it can be carried out. The second process now for its part claims the corresponding group of valves to provide the desired flow path. Accordingly, now only the second process can also make a decision on a further query of another process on the extent to which the valves claimed by it will be released again.

An extremely flexible control of the valves by which all the valves of the system can be used to the optimum thus results from the method in accordance with the invention for the control of the valves for the fluid path control. The valves in this connection represent a resource for the flow paths to be formed since a flow path is described by an arrangement of open and closed valves. A flow path can therefore only be carried out when all the resources are available, that is when all the valves participating in the flow path are available for the corresponding process.

The valve control in accordance with the invention permits the effective scheduling of the available resources in that it provides individual functionalities to the individual processes. A process for the provision of a flow path can request resources, that is claim available valves for itself, whereby they are no longer available to other processes, or release valves claimed for themselves again, whereby they are again available to other processes. Furthermore, individual processes can query the cancellation of another flow path (signaling) in order thus to claim required valves for itself. Processes can equally poll whether the flow path established by it should be cancelled (flow path status), e.g. because other processes have a higher priority. The decision on the cancellation of the flow path or on the release of the valves participating therein, however, is always made by the process which is utilizing the resources to be released.

A possibility which is simple to implement hereby results of synchronizing a plurality of processes with one another, e.g. to control a plurality of pumps, without impairing the safety of the total system.

The logic of the safety system of the treatment machine in accordance with the invention is also inverted for the described flexible flow path scheduling. In this connection, all the allowed flow paths are no longer stored which would then have to be revised on a change or a new introduction of a process, but rather all the prohibited paths are determined and stored at one time for the total arrangement of the valves, pumps and connections.

The present invention has a method for the monitoring of the state of the valves in the flow path control for this purpose. All the valve states are monitored for this purpose. If a valve status changes or if a process plans a change in valve status, all the connections are determined which result from the then current or scheduled switching state of the valves. The connections established in this context are then compared with the predetermined number of non permitted connections to recognize non permitted connections and thus non permitted switching states.

To determine the connections which result from a switching state of the valves, all the open valves are virtually flooded, starting from one or more positions, and the result of the flooding is entered into a connection matrix. A check can now be made directly from the connection matrix produced in this manner whether a prohibited path stored with the protective system is used or should be used.

Figure 4:
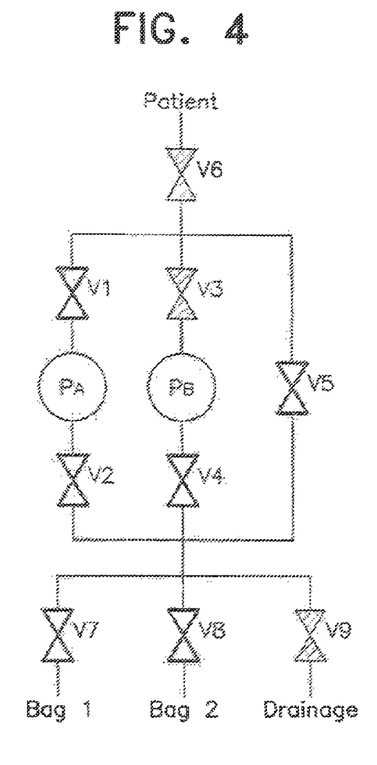
FIG. 4 is a first state of a plurality of valves which is monitored by an embodiment of the method in accordance with the present invention for monitoring valve states.

In this connection, a first switching state of the valves is shown in FIG. 4 in which the valves V3, V6 and V9 are open and the remaining valves are closed. The patient is hereby connected to the pump chamber Ps. This state corresponds to the connection matrix shown in FIG. 7 in which a connection is only present between the valve V3 and the valve V6. The likewise open valve V9 is not connected to any further open valves so that this open valve is no longer considered in the connection matrix.

Figure 5:
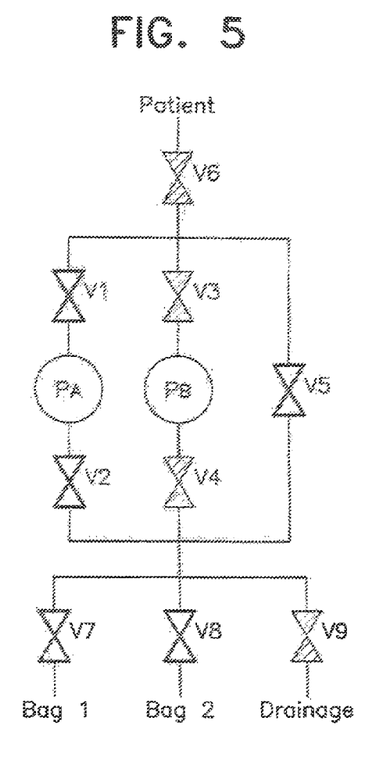
FIG. 5 is a second state of a plurality of valves which should be monitored by the embodiment of the method in accordance with the invention for monitoring valve states.

If now a change should be made from the switching state shown in FIG. 4 to the switching state shown in FIG. 5 in that the valve V4 is opened, the method in accordance with the invention for the monitoring of the scheduled state of the valves checks whether a non permitted connection hereby results.

Figure 8:
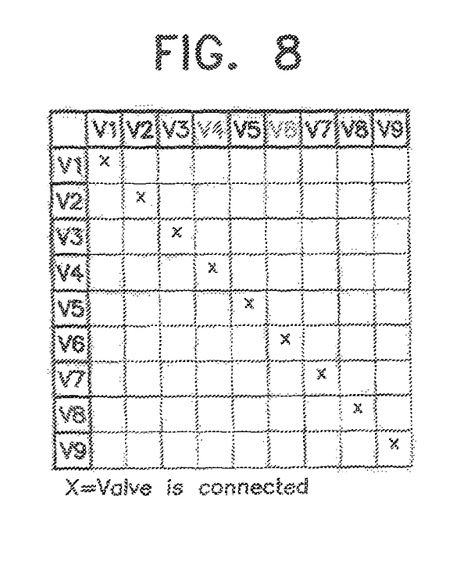
FIG. 8 is the starting point for a connection matrix as is prepared by the embodiment of the method in accordance with the invention for the monitoring of the state of a plurality of valves shown in FIG. 5.

In this connection, a still empty connection matrix is first assumed such as is shown in FIG. 8. By a virtual flooding of all open valves, all the connections which result from the state of the valves shown in FIG. 5 are now entered step by step. Connections between two valves Vx and Vy are marked in the connection matrix by an entry in the field of the matrix associated with the combination of the valves Vx and Vy. For the sake of clarity, connections are only shown in the bottom left half of the matrix in the connection matrices shown in FIGS. 7 to 9. The fields in the top right half are equivalent thereto.

The method for the determination of the connections arising from a switching state of the valves by means of a virtual flooding will now be described with reference to FIGS. 6*a* to 6*d* as well as to the associated resulting connection matrices 9*a* to 9*d*.

Figure 6:
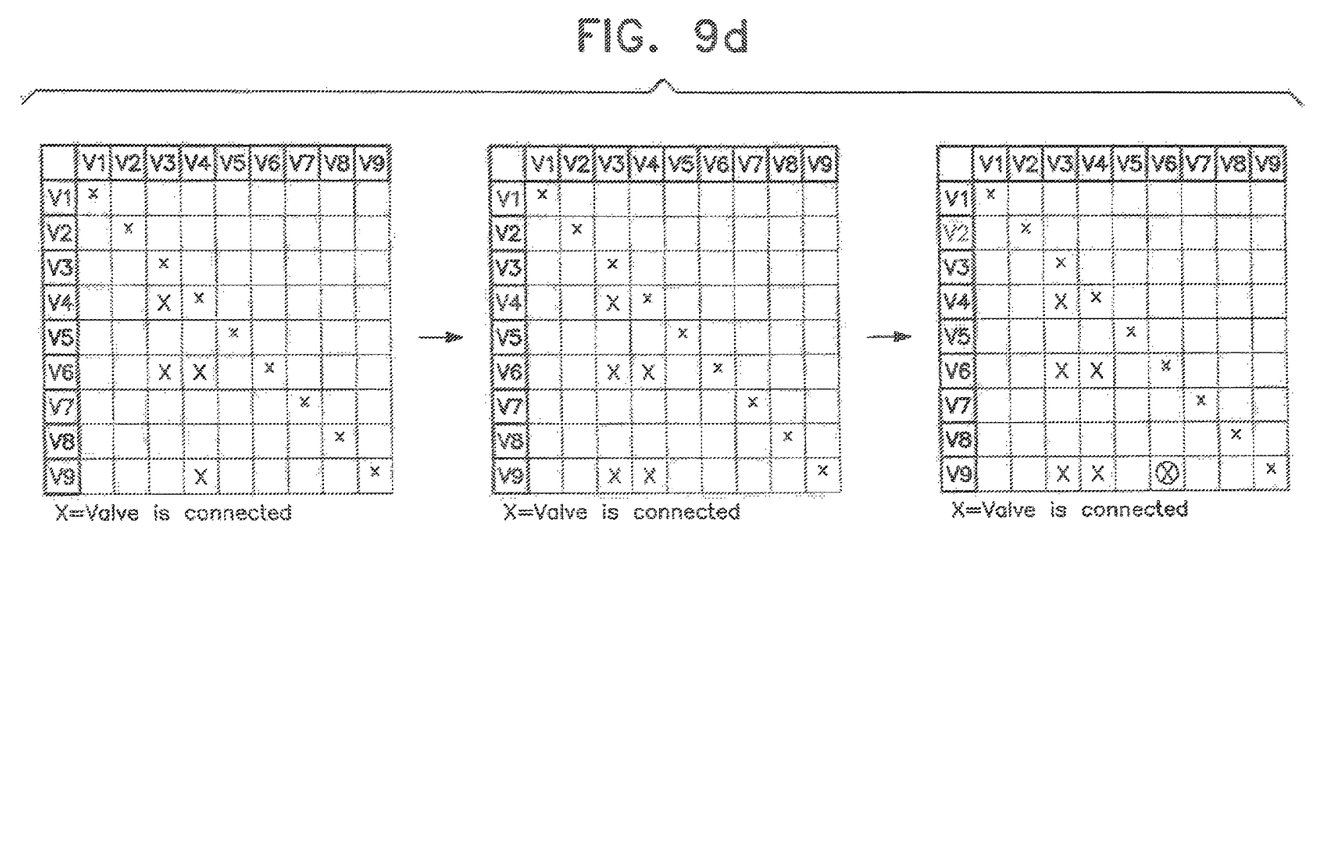
FIGS. 6a-6d are individual steps of the embodiment of the method in accordance with the present invention for the monitoring of a state.
Figure 6A:
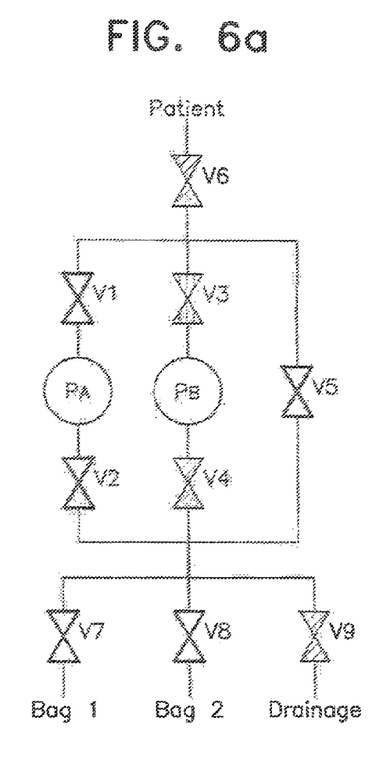
Figure 6B:
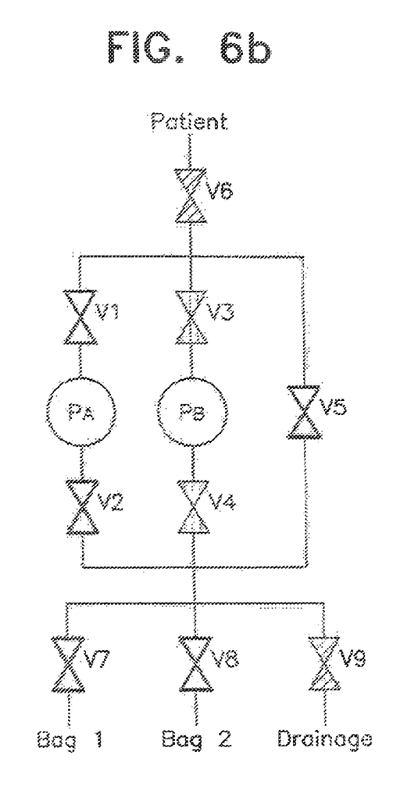
Figure 6C:
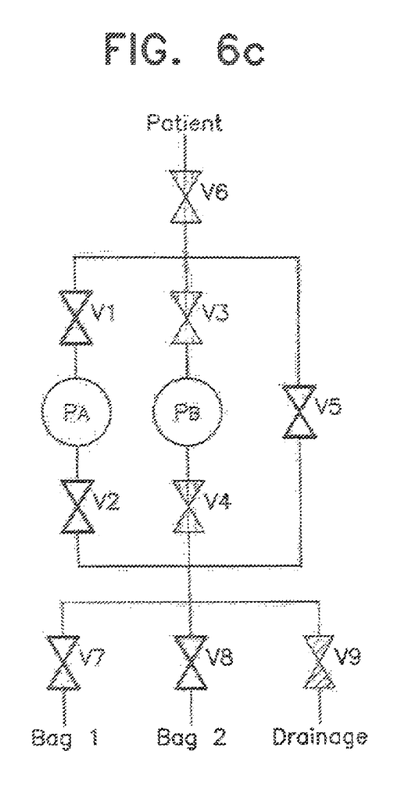
Figure 9A:
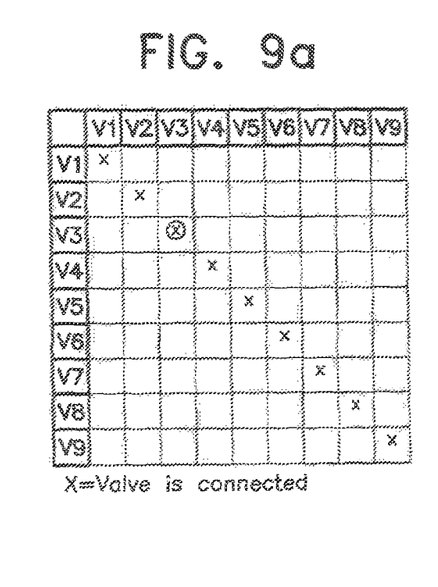

For this purpose, first a still not flooded, open valve is selected and virtually flooded in the state of the valves shown in FIG. 5. In the example shown, as illustrated in FIG. 6*a*, the valve V3 is first flooded. The corresponding selection is shown in FIG. 9*a* by the circling of the field in the connection matrix associated with the valve V3 itself. Starting from the valve V3 and as shown in FIGS. 6*b* and 6*c*, all the open valves adjacent to the valve selected as the starting point are flooded. The valve V4 is therefore flooded in FIG. 6*b* and valve V6 in FIG. 6*c*.

Figure 9B:
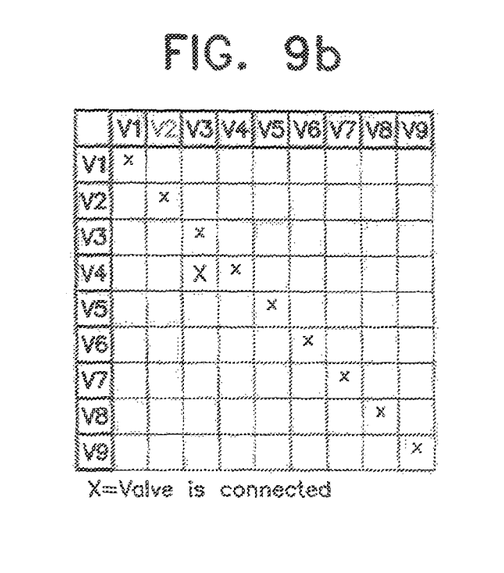
Figure 9C:
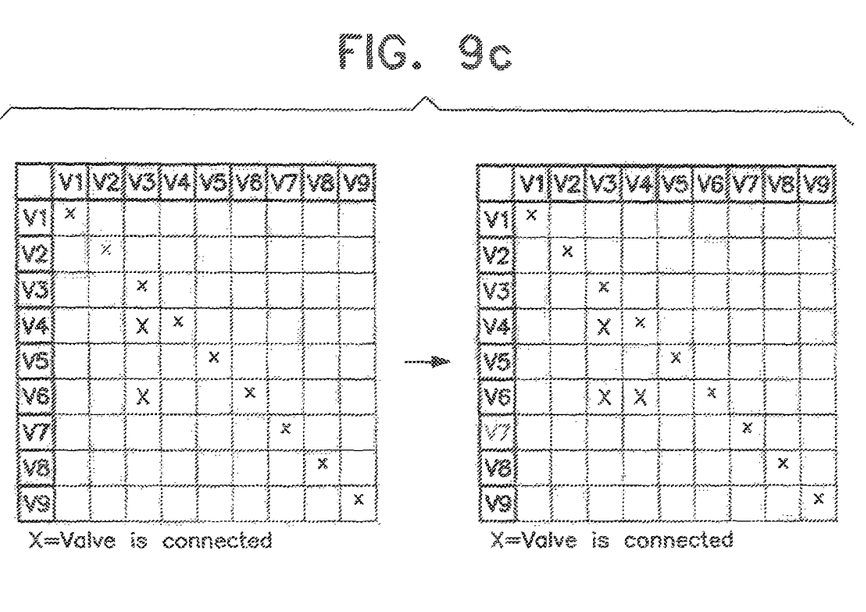

The connections resulting from this flooding are stored in the connection matrix. As shown in FIG. 9*b*, the connection established by flooding the valve V4 between the valves V3 and V4 is thus first stored in the connection matrix by a marking of the corresponding field. A connection is now first produced by the flooding of the valve V6 likewise adjacent to the valve V3 shown in FIG. 6*c* between the valves V3 and V6 which is first entered in the first connection matrix shown in FIG. 9*c*. The system now checks whether further connections between valves are produced by this new connection. In the embodiment, a connection is produced in this context by the connection of the valve V3 to the valve V6, on the one hand, and to the valve V4, on the other hand, between the valve V6 and the valve V4, said connection now being entered in a second step, as shown in second in FIG. 9c, into the connection matrix.

Figure 6D:
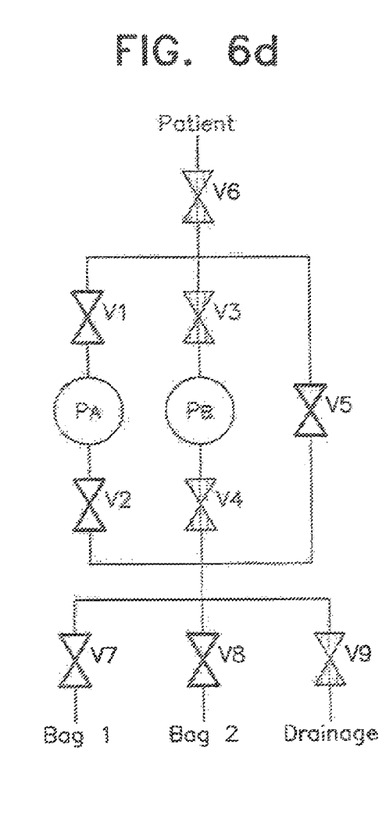
Figure 7:
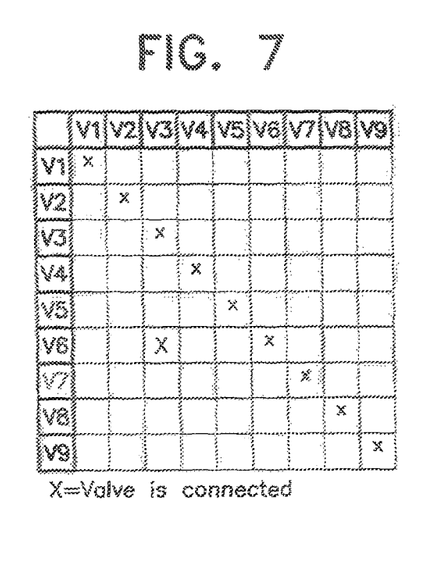
FIG. 7 is a connection matrix which is used in the embodiment of the method in accordance with the present invention for the monitoring and which corresponds to the state of a plurality of valves shown in FIG. 4.

The method now continues to flood further open valves adjacent to the already flooded valves. In this connection, no further open unflooded valve is adjacent to the valve V6 so that the method ceases here. The open valve V9 still unflooded in FIG. 6c, in contrast, is adjacent to the flooded valve V4 and is now likewise flooded in the next step which is shown in FIG. 6d. A connection between the valve V4 and the valve V9 hereby first results which is now entered into the connection matrix in a first step. This is illustrated in the first connection matrix shown in FIG. 9d. However, due to the already present connection between the valve V4 and V3, the new connection between the valve V9 and V3 is now also produced which is now entered into the connection matrix in a second step. Furthermore, due to the already present connection between the valve V6 and the valve V3 or the valve V4, a new connection is produced between the valve V9 and the valve V6 which is now likewise entered into the connection matrix in the last step.

After all the open valves connected to the valve selected as the starting point have been flooded and all the connections generated thereby have been entered into the connection matrix, the system checks whether further open valves which are still unflooded are present. If the system finds such a valve, it is selected as the starting point for a further virtual flooding which runs according to the same pattern. The system repeats this procedure for so long until all the open valves have been flooded.

All the connections which are produced by the examined state of the valves have now been entered in the connection matrix resulting from this virtual flooding.

The connection matrix is now compared with a control matrix in which all the non permitted connections have been entered. Such a control matrix e.g. includes the non permitted connection between the valves V9 and V6 by which a connection would be established between the patient and the drainage. The method in accordance with the invention thus recognizes, with reference to the connection matrix which is shown at the far right in FIG. 9d and which is determined for the state shown in FIG. 5, that a non permitted connections would be established by this state. Accordingly, the safety system in accordance with the invention prevents a switch being made into this state. If, in contrast, a then current switching state is checked by the safety system and it is found that a non permitted connection is present, the system automatically switches into a safe state.

In this connection, only non permitted connections have to be given between the terminals, i.e. between the valves V6 to V9. How these connections are realized is, in contrast, not relevant to the evaluation. All the permitted switching states of all valves thus no longer have to be stored in the safety system, but rather only the non permitted connections between terminals, whereas the system independently checks whether a specific switching state results in such a non permitted connection. It would be conceivable to store the permitted connections between the terminals in the safety system alternatively to the non permitted connections. All the permitted switching states would then also not have to be stored in the system. Since, however, considerably more permitted connections than non permitted connections are present, the storing of the non permitted connections is more effective.

The present invention furthermore includes, in addition to the shown embodiments of the methods, a treatment machine, in particular for peritoneal dialysis, in whose control the corresponding methods are implemented. The present invention furthermore includes a computer program product, in particular a storage medium, on which corresponding control software is stored which can be transferred to corresponding treatment machines to implement the methods in accordance with the invention there.

The invention being thus described, it will be apparent that the same may be varied in many ways. Such variations are not to be regarded as a departure form the spirit and scope of the invention, and all such modifications as would be recognized by one skilled in the art are intended to be included within the scope of the following claims.

What is claimed is:

1. A method for controlling valves for flow path control in a dialysis machine, having a plurality of processes for establishing a plurality of flow paths by controlling a plurality of valves that, before being claimed by a particular process, are available to, and controllable by, more than one process, each process being configured to provide a specific flow path and able to claim, release and poll valves required for establishing said specific flow path, wherein a process can claim different groups of valves from within said plurality of valves depending on an availability of the valves, for providing said specific flow path, said method comprising the steps of:

a first process for establishing a first flow path, the first process claiming a first group of valves from said plurality of valves, said claimed first group of valves being non-available to other processes while said first group of valves is claimed by said first process and other processes being unable to change a switching state of said first group of valves while said first group of valves is claimed by said first process;

executing the first process by setting switching states of said first group of valves, said switching states creating connections between the valves to establish said first flow path;

a second process for establishing a second flow path, the second process claiming a second group of valves from said plurality of valves, said claimed second group of valves being non-available to other processes while said second group of valves is claimed by said second process and other processes being unable to change switching states of said second group of valves while said second group of valves is claimed by said second process, and said second process is executed by setting the switching states of said second group of valves, said switching states creating connections between the valves to establish said second flow path;

polling by said second process before said second process is executed, whether the second group of valves suitable for establishing the second flow path is available for establishing the second flow path;

wherein in case that the second croup of valves includes a first valve out of said first group of valves claimed by said first process for establishing the first flow path and therefore is unavailable to the second process, the step of polling by said second process resulting in sending of a request to the first process for a release of said non-available first valve, said first process itself making a decision on said request for the release of the non-available first valve claimed by said first process;

once the first valve is released by the first process, the second process claiming the first valve, such that the first valve forms part of said second group of valves claimed by the second process and is non-available to other processes; and said second process being executed when all valves of the second group of valves are available and claimed by the second process.

2. The method in accordance with claim 1, wherein each process makes a decision on the release of the valves claimed by it in dependence on at least one of internal and external process criteria.

3. The method in accordance with claim 1, wherein each process releases the claimed group of valves after execution is complete.

4. The method in accordance with claim 1, wherein each process polls the availability of a group of valves suitable for executing a process before executing said process.

5. The method in accordance with claim 1, wherein a process is carried out when a suitable group of valves is available, with the process claiming said suitable group of valves for itself.

6. The method in accordance with claim 1, wherein a plurality of connections resulting from different switching states of the valves is determined by virtually flooding open valves from at least one starting point and storing resulting connections in a connection matrix.

7. The method in accordance with claim 1, further comprising the step of comparing the connections defining said first and second flow paths with a plurality of connections previously identified as non-permitted connections.

8. The method in accordance with claim 7, wherein a process identified as creating a non-permitted connection is not executed.

9. The method in accordance with claim 7, wherein in a presence of a non-permitted connection, the machine going into a safety state in which the switching states identified as creating a non-permitted connection are prevented.

10. The method in accordance with claim 7, wherein the step of comparing connections with a plurality of previously identified connections includes comparing a connection matrix with a control matrix that contains non-permitted connections.

11. The method in accordance with claim 7, wherein the current and scheduled switching states of the valves are monitored during performance of said plurality of processes to avoid a flow path having a non-permitted connection.

12. The method in accordance with claim 1, further comprising a central valve association process in which all of said plurality of processes are able to claim, release and poll required valves.

13. A dialysis machine having a plurality of processes for establishing a plurality of flow paths comprising:

a plurality of valve actuators for controlling valves to establish flow paths, said valve actuators in said plurality of valve actuators, before being claimed by a particular process, being available to, and controllable by, more than one process;

a valve actuator control for executing a plurality of processes for establishing said flow paths by controlling a group of said plurality of valve actuators;

the valve actuator control being configured such that each process provides a specific flow path and is able to claim, release and poll valve actuators required for establishing said specific flow path, and such that a process can claim different groups of valve actuators from within said plurality of valve actuators depending on an availability of the valve actuators, for providing said specific flow path;

the valve actuator control being further configured such that a first process polls an availability of a first group of valve actuators from said plurality of valve actuators to establish a first flow path suitable for said first process to execute a first one of said plurality of processes;

said first process being configured to control said first group of valve actuators that are determined to be available for execution of said first one of said plurality of processes, said first process claiming and setting switching states for said first group of valve actuators, said switching states creating connections between the valve actuators to establish the first flow path;

said claimed valve actuators being unavailable to other processes while said valve actuators are controlled by said first process and other processes being prevented from changing the switching states of said claimed group of valve actuators;

said valve actuator control being further configured such that a second process is able to poll valve actuators for controlling a second group of valves for establishing a second flow path;

wherein in case that the second group of valve actuators includes a first valve actuator cut of said first group of valve actuators claimed by said first process for establishing the first flow path and therefore is unavailable, to the second process, the step of polling by said second process resulting in sending of a request to the first process for a release of said non-available first valve actuator, said first process itself making a decision on said request for the release of the non available first valve actuator claimed by said first process;

said valve actuator control being configured such that, once the first valve actuator is released by the first process, the second process claims the first valve actuator, such that the first valve actuator forms part of said second group of valve actuators claimed by the second process and is non-available to other processes; and said valve actuator control being configured such that said second process is executed when all valve actuators of the second group of valve actuators are available and claimed by the second process.

14. The dialysis machine of claim 13, wherein said machine is configured to compare the connections that define said first flow path with a plurality of connections previously identified as non-permitted connections, said machine upon detection of a non-permitted connection being further configured to stop said first process from execution of said first flow path.

15. The dialysis machine of claim 14, wherein said machine is configured, upon detection of a non-permitted connection, to enter a safety state in which the switching states identified as creating the non-permitted connection are prevented.

16. The dialysis machine of claim 13, wherein said machine is configured to monitor the current and scheduled switching states of the valve actuators to avoid a non-permitted connection.

17. The dialysis machine in accordance with claim 13, wherein each process makes a decision on release of the valve actuators claimed by it in dependence on at least one of internal and external process criteria.

18. The dialysis machine in accordance with claim 13, further comprising:

a connection matrix for storing a plurality of connections resulting from a valve actuator switching state; and a control matrix containing non-permitted connections;

said machine being configured to compare the connection matrix with the control matrix when establishing a flow path to avoid switching states that result in use of a non-permitted connection.

19. The dialysis machine in accordance with claim 13, wherein each process releases the claimed group of valve actuators after execution is completed.

20. The dialysis machine in accordance with claim 13, wherein each process polls for availability of a group of valve actuators suitable for execution of a process before execution thereof.

21. The dialysis machine in accordance with claim 13, wherein each process polling for valve actuators receives a claiming right, for all polled but not available valve actuators on the polling so that the process that is polling can claim these valve actuators for itself when said polled but not available valve actuators have been released.

22. The dialysis machine in accordance with claim 13, wherein the valve actuator control includes a central valve association process in which all the other processes are able to claim, release and poll required valve actuators.

23. The dialysis machine in accordance with claim 11, wherein said machine has a machine side with a coupling surface for coupling of a cassette, said cassette including valves and liquid conducting passages, wherein the valve actuators on the machine side determine a switching state of the valves on the cassette to establish different flow paths.

\* \* \* \* \*